United States Patent [19]
Atkinson

[11] Patent Number: 5,505,708
[45] Date of Patent: Apr. 9, 1996

[54] SYSTEM FOR DELIVERY OF INTRAVENOUS FLUIDS AND THE LIKE AND THE METHOD OF MAKING THEREOF

[76] Inventor: Carey J. Atkinson, 225 Boundary Rd., Suite C, Wasilla, Ak. 99654

[21] Appl. No.: 229,182

[22] Filed: Apr. 18, 1994

[51] Int. Cl.$^6$ .................................................. A61M 5/155
[52] U.S. Cl. .................................... 604/140; 604/410
[58] Field of Search ................................ 604/140, 141, 604/142, 143, 144, 145, 146, 147, 410, 408

[56] References Cited

U.S. PATENT DOCUMENTS

| | | | |
|---|---|---|---|
| 3,023,250 | 3/1962 | Baron | 604/145 |
| 3,838,794 | 10/1974 | Cogley et al. | 604/141 |
| 3,871,518 | 3/1975 | Murray et al. | 604/145 |
| 4,235,233 | 11/1980 | Mouwen | 604/410 |
| 4,396,382 | 8/1983 | Goldhaber | 604/410 |
| 4,396,383 | 8/1983 | Hart | 604/410 |
| 4,551,136 | 11/1985 | Mandl | 604/141 |
| 4,673,392 | 6/1987 | Keime | 604/141 |
| 4,826,244 | 12/1986 | Reinicke | 604/141 |
| 4,994,039 | 2/1991 | Mattson | 604/410 |
| 5,135,499 | 8/1992 | Tafani et al. | 604/140 |
| 5,163,909 | 11/1992 | Stewart | 604/140 |

*Primary Examiner*—Paul J. Hirsch
*Attorney, Agent, or Firm*—Michael J. Tavella

[57] ABSTRACT

A new intravenous fluid delivery system is disclosed. It consists of an inner product containment envelope that is covered on both sides by outer pressure envelopes. The seams of both the inner and outer envelopes are sealed together along their perimeters resulting in the outer envelopes forming a double wall around the inner product envelope. An outlet port is provided for the product containment envelope for removal of the fluids. This outlet port is similar to those found on common IV bags. A second pressure entry port is provided opposite to the outlet port. The second entry port is in communication with both outer pressure envelopes. Thus, as pressure is induced into the pressure entry port, product will be forced out of the outlet port once it is opened. As pressure in added to the outer envelopes, the inner envelope will be compressed, continuously draining the product within the product envelope until it is evacuated. Because pressure is being supplied to the outer envelopes uniformly, product will be forced out of the inner envelope regardless of the position of the invention. Thus, the invention can be placed horizontally and fluid will still flow as long as pressure is maintained in the outer envelopes. Because title inner product envelope is connected to the outer envelopes continuously along the seams, it cannot separate and collapse while leaving product in the inner envelope.

11 Claims, 5 Drawing Sheets

5,505,708

SYSTEM FOR DELIVERY OF INTRAVENOUS FLUIDS AND THE LIKE AND THE METHOD OF MAKING THEREOF

This invention relates to intravenous fluid bags and more particularly to intravenous fluid bags having a pressurized evacuation means for forcing fluid from a bag using diametrically opposed pressure waves.

BACKGROUND OF THE INVENTION

One of the most common tools found in modern medicine is the intravenous fluid bag or IV bag. These bags are used to dispense medicine and fluids (e.g., water, saline solution, etc.) under many different conditions. Originally, IV "bags" were glass bottles. Modern bags are made of soft plastic. Traditionally, gravity has been used to drain the fluid from the bag. The common view of an IV bag suspended from a pole above a patient's bed is a familiar sight. Pictures of soldiers holding IV bags over wounded soldiers are also a common sight. Therein lies the problem with these bags. There is no practical way to drain the standard IV bag without gravity or a mechanical pump. In combat, this is an especially serious problem because it requires a person to do nothing but hold a bag. The same is true for paramedics, who are forced to work frequently in field conditions.

Mechanical pumps now exist to drain bags, but these are operated electrically and are most convenient in a hospital setting. Moreover, pumps must be monitored to ensure that proper dosages and fluid flows are maintained. The level of maintenance for these pumps is often little improvement over the standard gravity bags. Also, IV pumps are extensive.

The present invention overcomes these difficulties. It consists of a double walled envelope that evacuates the fluid within the envelopes by pressure waves. The action of the pressure waves operates on the fluid regardless of the position of the IV envelope. Thus, the envelope can be set down on a stretcher or on the patient and the product will still be delivered. It is important to understand that this double walled envelope is not a "bag within a bag". A bag within a bag design would have an inner product bag that is surrounded by an outer pressure bag. It is true that as air pressure is forced into the outer bag, the pressure created forces product from the inner bag. The problem with this design, however, is that in many positions, the inner bag is choked off by the pressure in the outer bag before all of the product can be removed. This is because the inner and outer bags are not connected completely around their perimeters, air is free to move around the inner bag, moving it away from the walls of the outer bag which often squeezes the outlet valve, shutting down the flow of fluid.

In the present invention, the IV envelope system is formed by creating an inner product containment envelope that is covered on all sides by outer pressure envelopes. The seams of both the inner and outer envelopes are sealed together along their perimeters resulting in the outer envelopes forming two walls around the inner product envelope.

An outlet port is provided for the product containment envelope for removal of the fluids. This outlet port is similar to those found on common IV bags. A second pressure entry port is provided opposite to the outlet port. The second entry port is in communication with both outer pressure envelopes. Thus, as pressure is induced into the pressure entry port, product will be forced out of the outlet port once it is opened. As pressure is added to the outer envelopes directionally, the inner envelope will be compressed and will continuously force product out the envelope out until it is evacuated. Because pressure is being supplied to the outer envelopes uniformly, product will be forced out of the inner envelope regardless of the position of the invention. Thus, the IV envelope can be placed horizontally and fluid will still flow as long as pressure is maintained in the outer envelopes.

Because the inner product envelope is connected to the outer envelopes continuously along the seams, it cannot separate and collapse While leaving product in the inner envelope, which can occur with a "bag within a bag" design.

It is an object of this invention to produce an IV delivery system that can operate at all angles.

It is another object of this invention to produce an IV system that can operate without gravity feed.

It is yet another object of this invention to produce an IV system that can operate at all aspects.

It is as yet another object of this invention to produce an IV system that can operate in all types of weather conditions.

DETAILED DESCRIPTION OF THE INVENTION

Figure 1:
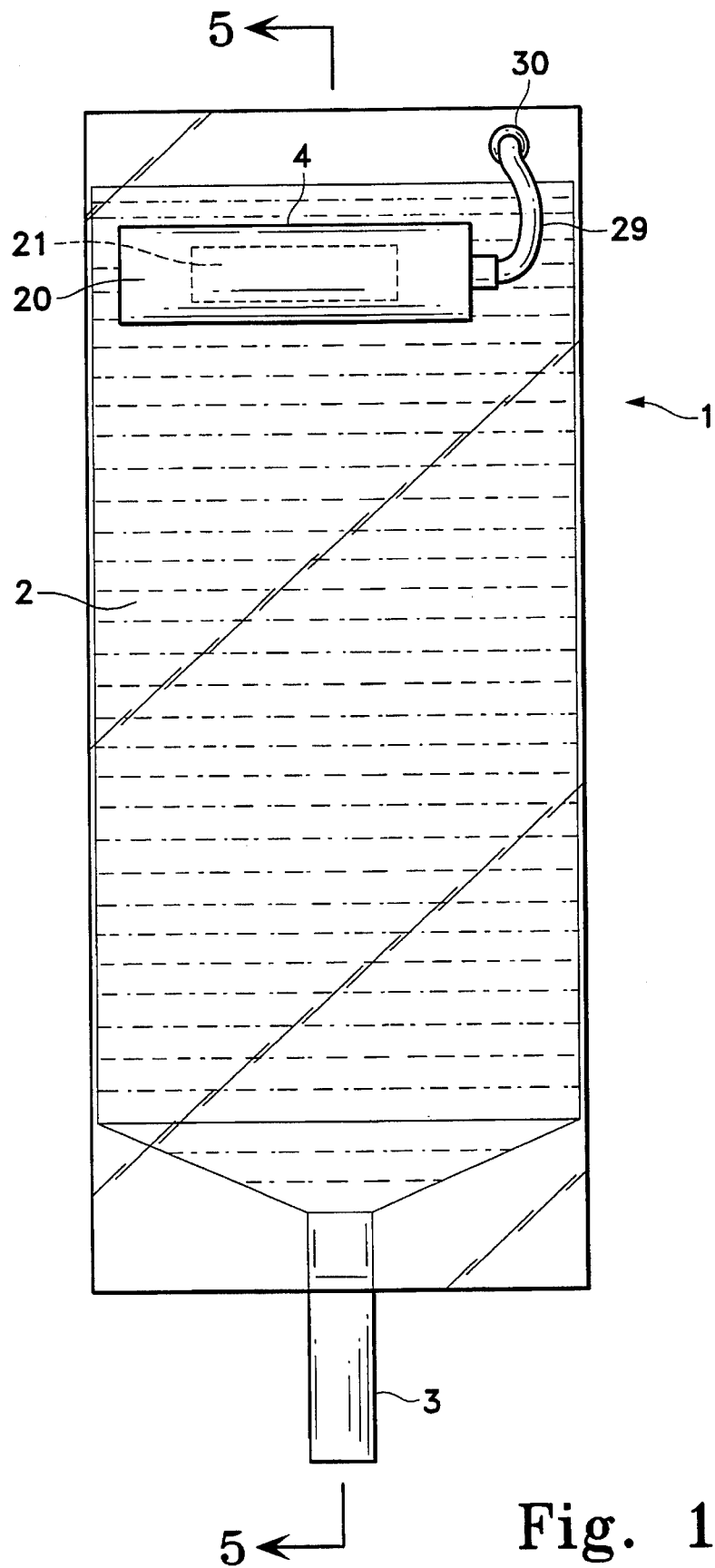
FIG. 1 is a side view of the invention with the product envelope full of fluid.
Figure 2:
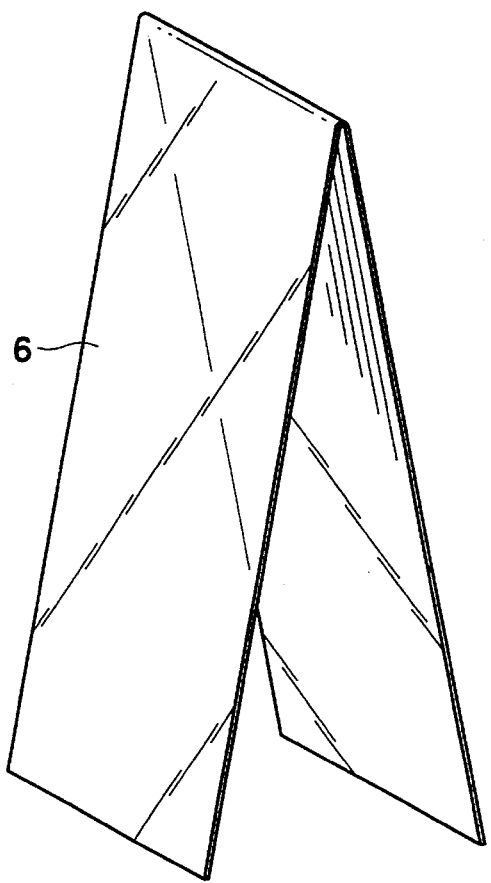
FIG. 2 is a perspective view of a typical envelope formation.
Figure 3:
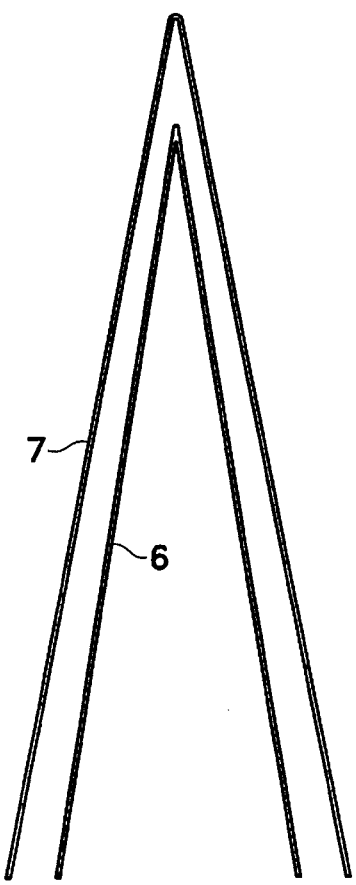
FIG. 3 is a side view of the inner product envelope positioned within the outer pressure envelope prior to sealing.
Figure 5:
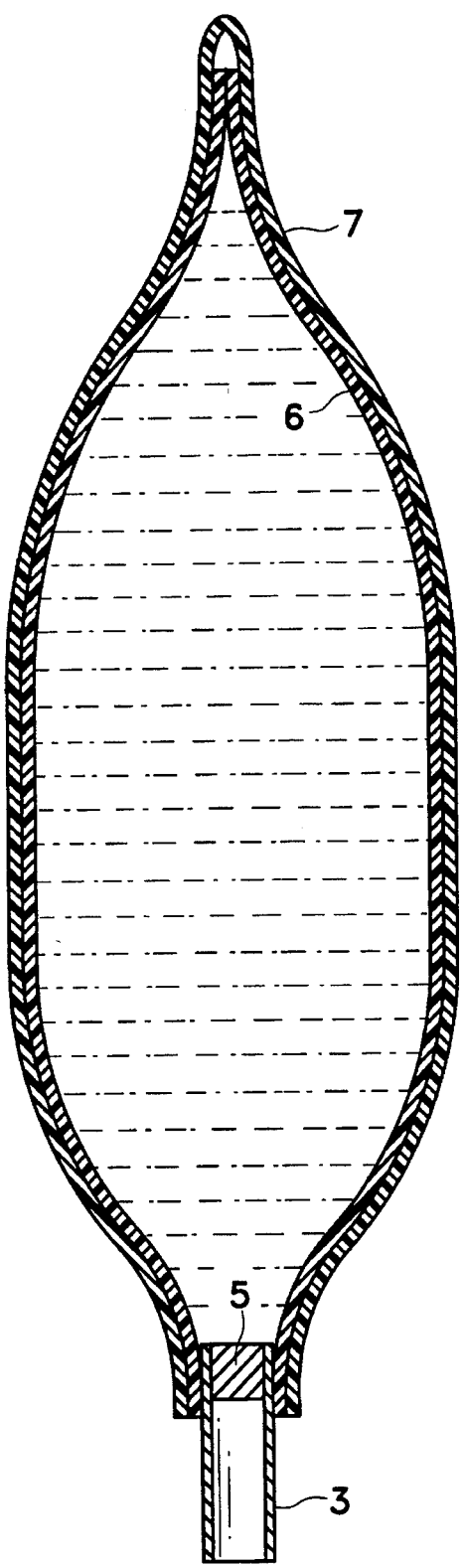
FIG. 5 is a cross-sectional view along the lines 5—5 of the envelope system.
Figure 6:
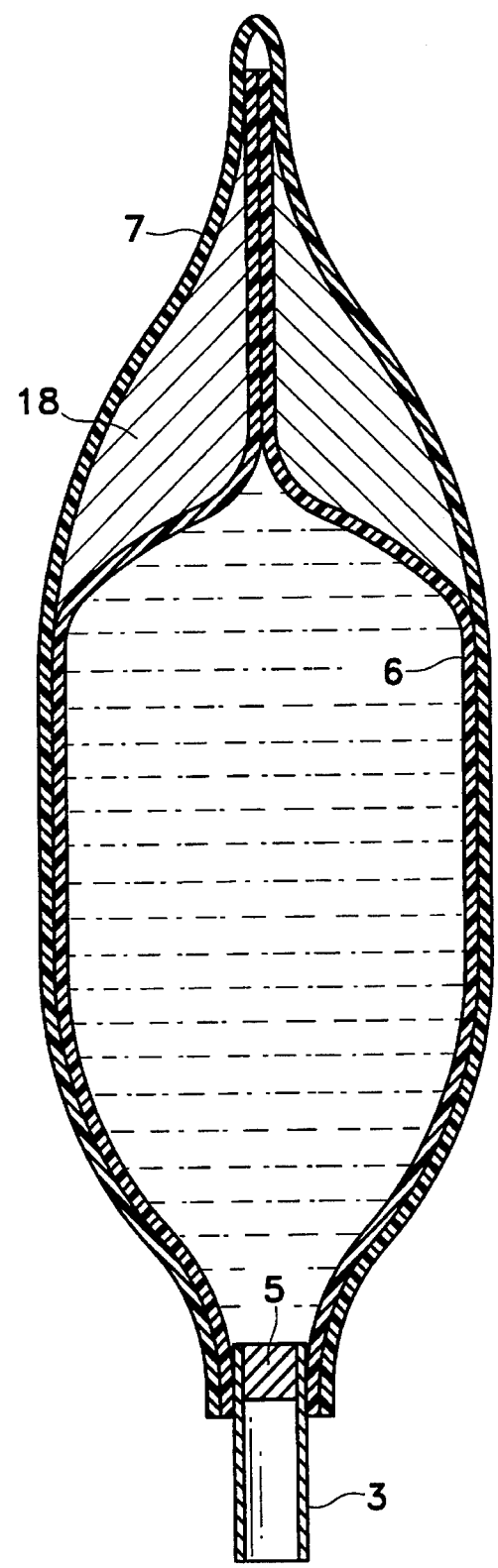
FIG. 6 is a cross-sectional view along the lines of FIG. 5 of the envelope system, showing a partially evacuated product containment envelope.
Figure 7:
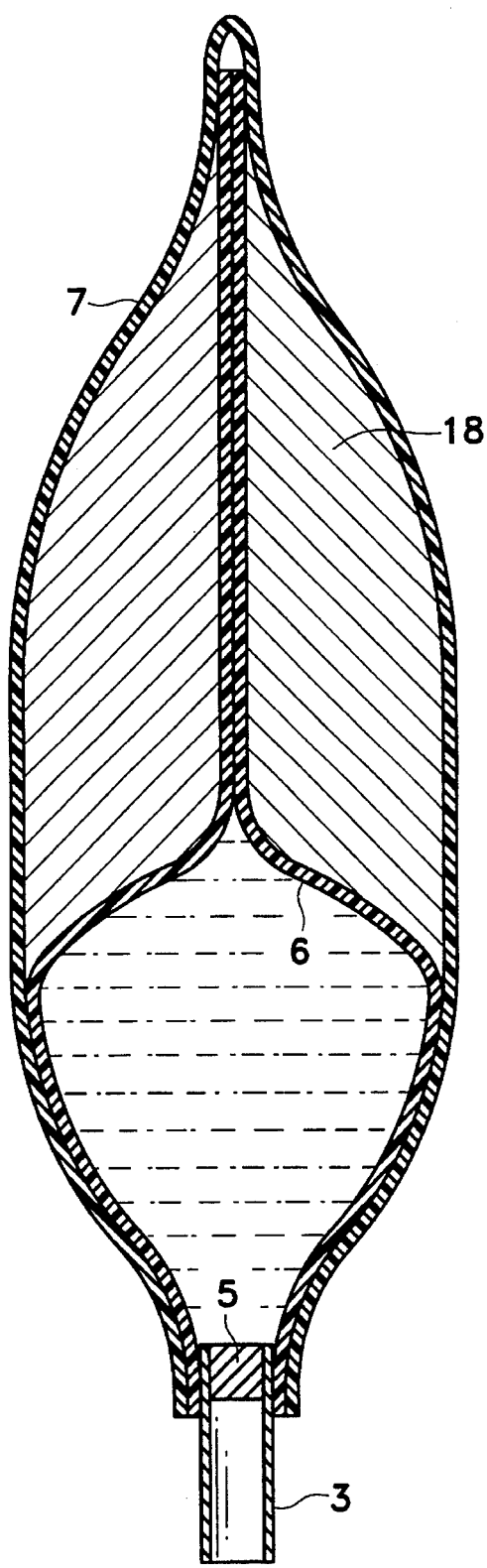
FIG. 7 is a cross-sectional view along the lines of FIG. 5 of the envelope system, showing the product containment envelope at a later stage of evacuation.
Figure 8:
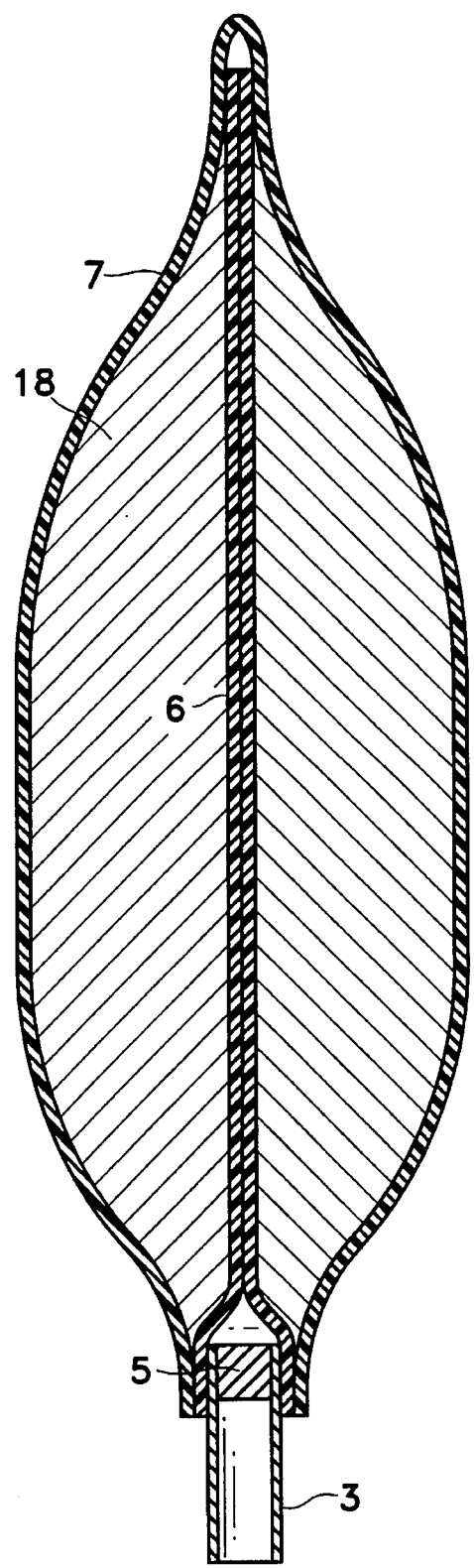
FIG. 8 is a cross-sectional view along the lines of FIG. 5 of the envelope system, showing the product containment envelope completely evacuated.

FIG. 1 is a side view of the invention 1. The IV envelope system has a fluid carrying assembly 2, an exit port 3 and an inflation system 4. Valves 5 (see e.g., FIG. 5) prevent the escape of fluid until such time as the fluid is needed. The valve 5 is typically seated within the exit port 3 and is common to the art. This valve is typically just a plug that can be pierced with a needle or other sharp instrument. The fluid carrying assembly 2 consists of an inner product envelope 6 and an outer pressure envelope 7. Both envelopes 6 and 7 are formed of plastic common to the art. The inner product envelope 6 is formed from one piece of material that is folded. Once folded, the inner envelope 6 is placed within the outer pressure envelope 7 as shown in FIG. 3. The outer pressure envelope 7 is also a piece of folded plastic sheeting. The edges of both envelopes than then be sealed around their perimeters. In practice, a sheets several feet long can be used. Once the sheets are folded, the outer edge seam can be sealed. After that, the envelopes can be sealed and cut simultaneously in one operation, with the seamers and cutters set to match the desired width of the envelopes.

Figure 4:
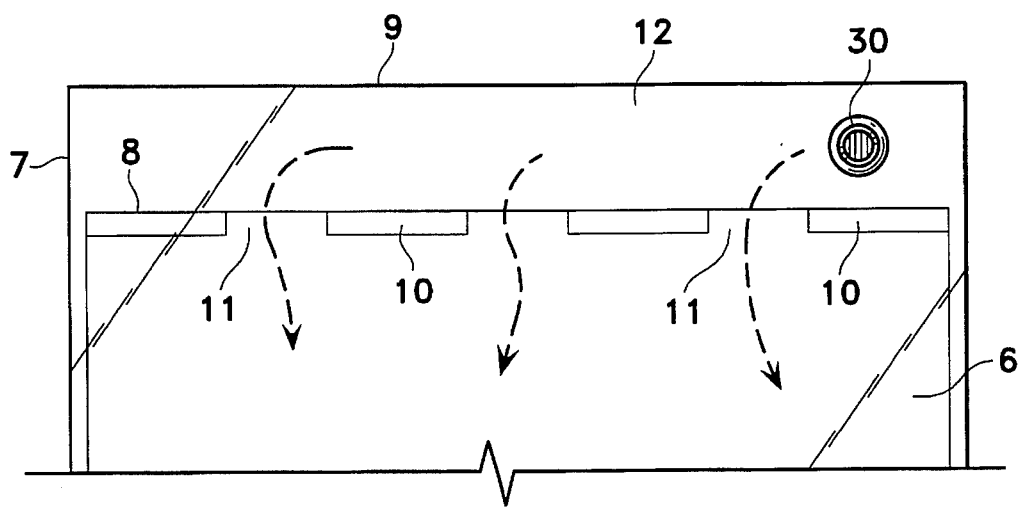
FIG. 4 is a detail of the top seam showing the flow of pressurizing gas.

FIG. 4 shows the method of creating the top seams. The product envelope 6 is placed within the outer pressure envelope 7 as shown. Note that the folded top edge 8 of the product envelope 6 does not go completely to the top folded edge 9 of the outer envelope 7. This gap creates an air chamber to permit the entrance of pressurized gas to flow. The top seams 10 are tacked together as shown. This secures the outer envelope 7 to the product envelope 6. Use of tacking creates gaps 11 through which the pressurized gas (arrows) can flow from the upper chamber 12 into the outer pressure envelope 7. The seam structure is identical on both sides of the device. This ensures that pressure will be supplied equally to the outer envelope 7.

FIG. 1 shows the inflation system 4. It consists of a small canister 20 of gas held under pressure And some means to secure the canister to the bag. In the preferred embodiment, this means is a small patch of VELCRO 21, a hook and eye fastener, that is attached to both the envelope and the canister 20. Use of the VELCRO patches allows the canister to be changed quickly. Canisters can be made for different temperatures, altitudes or barometric pressures. In this case, the proper canister can be installed on the envelope quickly and easily in the field.

Figure 9:
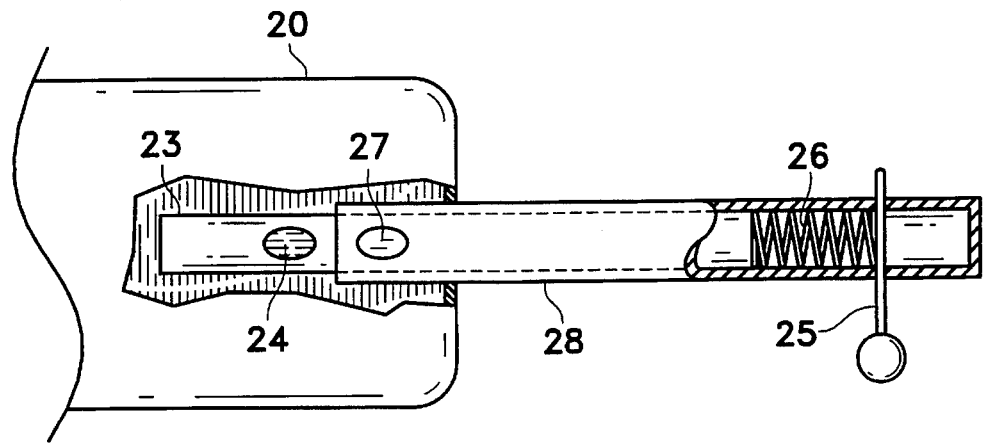
FIG. 9 is a cutaway detail view of the canister valve release mechanism in the closed position.
Figure 10:
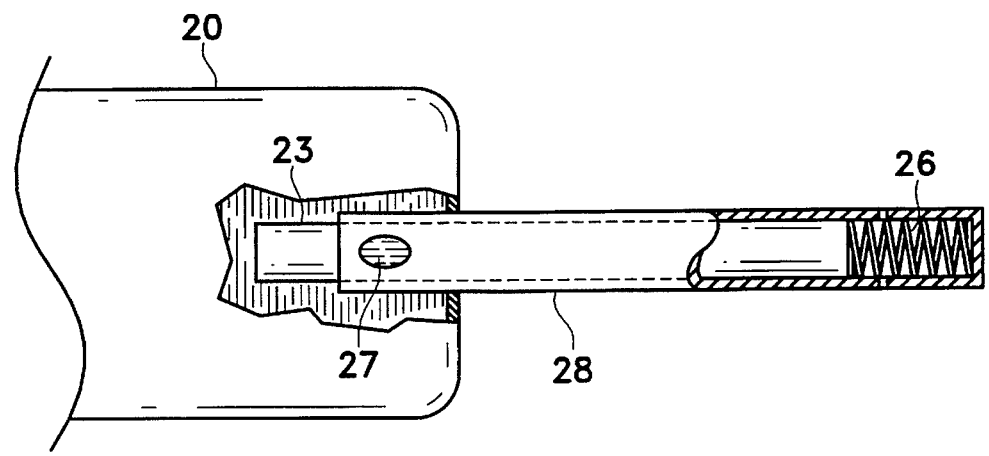
FIG. 10 is a cutaway detail view of the canister valve release mechanism in the open position.
Figure 11:
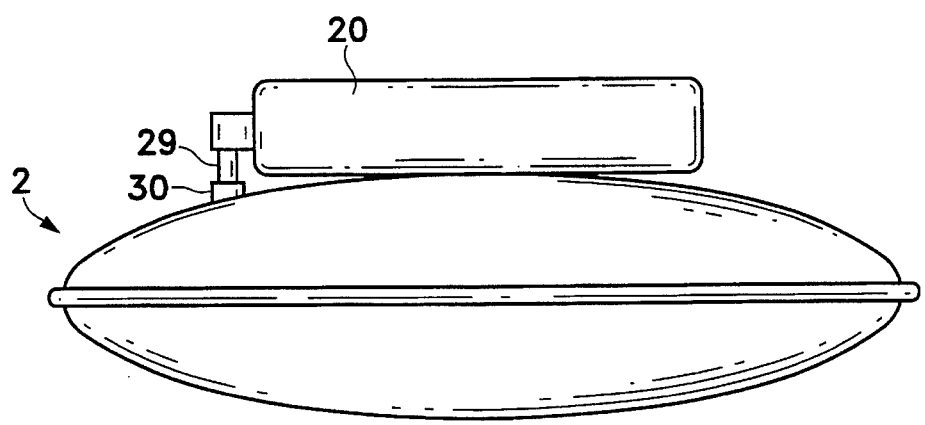
FIG. 11 is a top view of the device showing an alternative tube design for the canister.

The canister 20 has a valve system (see FIG. 9) that operates by means of a pin 25 when the pin 25 is pulled, a spring 26 releases, allowing the exit hole 27 in the outlet valve channels 28 to align with the exit hole 24 in the center plug channel 23 When that occurs the gas is released through holes 27 and 24, it enters a small hose or tube 29 to transport the gas from the canister into the envelope. FIG. 11 shows an alternative tube 29 that is rigid and forms a right angle to the canister, much like the outlet of a shaving cream type can.

A pressure valve 30 is provided on the envelope 7 as shown. This valve is identical to those found on many inflatable products such as air mattresses, beach balls, etc. As the gas is released from the canister, it flows into the valve 30 and proceeds to fill the outer pressure envelope 7. In the preferred embodiment, the maximum pressure from the canister should not exceed that pressure which would deliver the fluid at American Medical Association recommended pressures.

This system is designed to provide equal pressure to both sides of the outer pressure envelope. Referring now to FIGS. 5–8, as the gas enters the outer pressure envelope 7, the inner product envelope is compressed uniformly. As product evacuates, the inner product envelope 6 becomes squeezed flat. Because it is secured along the side seams, as it collapses, it remains centered within the outer product envelope. The gas flowing into the outer pressure envelopes creates a traveling pressure wave 18 (signified by the hatching in FIGS. 6, 7 and 8) that moves down the product envelope 6 until it is completely drained. Also, because of this design, the pressurizing gas will automatically flow into the outer pressure envelope that can most readily receive it. Thus, if the invention is suspended, both outer pressure envelopes will inflate uniformly. If the invention is placed horizontally, initially, the uppermost pressure envelope will receive the greatest volume of gas while the bottom pressure envelope will only slightly inflate. However, each side of the outer pressure envelope will be at the same pressure.

To use the invention, the IV envelope would be selected with the proper temperature canister. The IV tubing would be installed within the valve of the outlet port. The canister pin would be pulled and the gas would begin the evacuation process. Once started, the envelope system can be set down or hung where convenient and left to work by itself.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. An intravenous fluid storage and delivery system comprising:
   a) a product storage envelope being generally rectangular and having a top, a bottom, a front wall, a back wall and two oppositely disposed sides;
   b) an outer pressure envelope, also being generally rectangular and having a top, a bottom, a front wall, a back wall, and two oppositely disposed sides, said outer pressure vessel being placed so as to completely surround and cover said product storage envelope and further such that said bottom and sides of said outer pressure envelope being in continuous sealing contact with the bottom and sides of said product envelope such that a common seam exists around the perimeter of the envelopes;
   c) fluid means, sealably stored in said product envelope;
   d) outlet means in communication with said product storage envelope to enable extraction of said fluid means from said product storage envelope; and
   e) inlet means in communication with said outer pressure envelope to permit entry of external fluid or gaseous means into said outer pressure envelope.

2. The intravenous fluid storage and delivery system of claim 1 further comprising:
   a) a canister of gas removably connected to said inlet means; and
   b) valve means to control the flow of gas into said inlet means.

3. The intravenous fluid storage and delivery system of claim 2 further comprising means to removably attached said canister to said outer pressure envelope.

4. The intravenous fluid storage and delivery system of claim 1 wherein the flow of gas into said inlet means creates a traveling pressure wave within said outer pressure envelope.

5. The intravenous fluid storage and delivery system of claim 4 wherein said traveling pressure wave is delivered with equal pressure to both the front wall and the back wall of said inner product envelope.

6. The intravenous fluid storage and delivery system of claim 3 wherein said means to removably attach said canister to said outer pressure envelope comprise a hook and eye type faster.

7. An intravenous fluid storage and delivery system comprising:
   a) a product storage envelope being generally rectangular and having a top, a bottom, a front wall, a back wall and two oppositely disposed sides;

b) an outer pressure envelope, also being generally rectangular and having a top, a bottom, a front wall, a back wall, and two oppositely disposed sides, said outer pressure vessel being placed so as to completely surround and cover said product storage envelope and further such that said bottom and sides of said outer pressure envelope being in continuous sealing contact with the bottom and sides of said product envelope such that a common seam exists around the perimeter of the envelope and further such that the top of said outer pressure envelope is attached to said top of said inner product envelope with non-continuous seams and with a spatial gap therebetween, said non-continuous seams permitting the flow of gas or liquid from said spatial gap into said outer pressure envelope;

c) fluid means, sealably stored in said product envelope;

d) outlet means in communication with said product storage envelope to enable extraction of said fluid means from said product storage envelope;

e) inlet means in communication with said outer pressure envelope to permit entry of external fluid or gaseous means into said outer pressure envelope through said spatial gap;

f) a canister of gas removably connected to said inlet means; and b) valve means to control the flow of gas into said inlet means.

8. The intravenous fluid storage and delivery system of claim 7 further comprising means to removably attached said canister to said outer pressure envelope.

9. The intravenous fluid storage and delivery system of claim 7 wherein the flow of gas into said outer pressure envelope creates a traveling pressure wave within said outer pressure envelope.

10. The intravenous fluid storage and delivery system of claim 9 Wherein said traveling pressure wave is delivered with equal pressure to both the front wall and the back wall of said inner product envelope.

11. The intravenous fluid storage and delivery system of claim 8 wherein said means to removably attach said canister to said outer pressure envelope comprise a hook and eye type faster.

\* \* \* \* \*